(12) United States Patent
Ortmann et al.

(10) Patent No.: US 7,345,185 B2
(45) Date of Patent: Mar. 18, 2008

(54) METHOD FOR PRODUCING ORGANOACYLPHOSPHITES

(75) Inventors: Dagmara Ortmann, Brig (CH); Klaus-Diether Wiese, Haltern am See (DE); Oliver Moeller, Recklinghausen (DE); Dirk Fridag, Haltern am See (DE)

(73) Assignee: OXENO Olefinchemie GmbH, Marl (DE)

( * ) Notice: Subject to any disclaimer, the term of this patent is extended or adjusted under 35 U.S.C. 154(b) by 0 days.

(21) Appl. No.: 10/584,492

(22) PCT Filed: Oct. 27, 2004

(86) PCT No.: PCT/EP2004/052675

§ 371 (c)(1),
(2), (4) Date: Dec. 8, 2006

(87) PCT Pub. No.: WO2005/063781

PCT Pub. Date: Jul. 14, 2005

(65) Prior Publication Data

US 2007/0117995 A1      May 24, 2007

(30) Foreign Application Priority Data

Dec. 23, 2003 (DE) ................. 103 60 772

(51) Int. Cl.
*C07F 9/02* (2006.01)
(52) U.S. Cl. .......................... 556/404; 558/83
(58) Field of Classification Search ......... 556/404; 558/83
See application file for complete search history.

(56) References Cited

U.S. PATENT DOCUMENTS

| | | |
|---|---|---|
| 5,093,534 A | 3/1992 | Ludwig et al. |
| 6,015,928 A | 1/2000 | Gubisch et al. |
| 6,184,424 B1 | 2/2001 | Bueschken et al. |
| 6,239,318 B1 | 5/2001 | Schuler et al. |
| 6,331,657 B1 | 12/2001 | Kaizik et al. |
| 6,403,836 B2 | 6/2002 | Kaizik et al. |
| 6,403,837 B1 | 6/2002 | Hess et al. |
| 6,407,295 B1 | 6/2002 | Kaizik et al. |
| 6,482,992 B2 | 11/2002 | Scholz et al. |

(Continued)

FOREIGN PATENT DOCUMENTS

DE      100 53 272      5/2002

(Continued)

OTHER PUBLICATIONS

U.S. Appl. No. 11/574,063, filed Feb. 22, 2007, Nierlich, et al.

(Continued)

*Primary Examiner*—Yvonne (Bonnie) Eyler
*Assistant Examiner*—Chukwuma O. Nwaonicha
(74) *Attorney, Agent, or Firm*—Oblon, Spivak, McClelland, Maier & Neustadt, P.C.

(57) ABSTRACT

The present invention relates to a process for preparing organophosphites, organosphonites and organophosphinites by condensing phosphorus trihalides or organophosphorus halides with organic compounds bearing hydroxyl groups in the presence of polymeric basic ion exchange resins.

Figure 1:
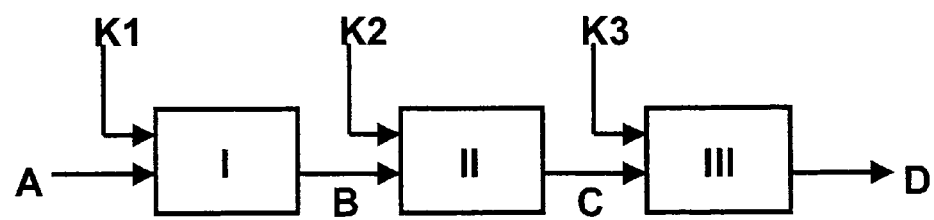

The process according to the invention makes possible in a simple manner the preparation of trivalent organophosphorus compounds which may serve, for example, as ligands in rhodium complexes which may be used as a catalyst in hydroformylation.

18 Claims, 1 Drawing Sheet

U.S. PATENT DOCUMENTS

| | | |
|---|---|---|
| 6,492,564 B1 | 12/2002 | Wiese et al. |
| 6,500,991 B2 | 12/2002 | Wiese et al. |
| 6,555,716 B2 | 4/2003 | Protzmann et al. |
| 6,570,033 B2 | 5/2003 | Roettger et al. |
| 6,627,782 B2 | 9/2003 | Kaizik et al. |
| 6,680,414 B2 | 1/2004 | Knoop et al. |
| 6,720,457 B2 | 4/2004 | Drees et al. |
| 6,818,770 B2 | 11/2004 | Selent et al. |
| 6,924,389 B2 | 8/2005 | Jackstell et al. |
| 6,956,133 B2 | 10/2005 | Jackstell et al. |
| 6,960,699 B2 | 11/2005 | Totsch et al. |
| 7,009,068 B2 | 3/2006 | Schmutzler et al. |
| 7,109,346 B2 | 9/2006 | Beller et al. |
| 2002/0111487 A1* | 8/2002 | Roettger et al. ............. 546/22 |
| 2003/0144559 A1 | 7/2003 | Hess et al. |
| 2003/0195368 A1 | 10/2003 | Rottger et al. |
| 2004/0236133 A1* | 11/2004 | Selent et al. ............... 558/153 |
| 2004/0236134 A1* | 11/2004 | Schmutzler et al. ........ 558/153 |
| 2004/0238787 A1 | 12/2004 | Wiese et al. |
| 2004/0242947 A1 | 12/2004 | Beller et al. |
| 2005/0043279 A1 | 2/2005 | Selent et al. |
| 2005/0171371 A1 | 8/2005 | Borner et al. |
| 2005/0182277 A1 | 8/2005 | Totsch et al. |
| 2005/0209455 A1 | 9/2005 | Boerner et al. |
| 2005/0209489 A1 | 9/2005 | Moller et al. |
| 2005/0234270 A1 | 10/2005 | Kaizik et al. |
| 2005/0256281 A1 | 11/2005 | Grund et al. |
| 2006/0036121 A1 | 2/2006 | Kaizik et al. |
| 2006/0089469 A1 | 4/2006 | Komarov et al. |
| 2006/0128998 A1 | 6/2006 | Lueken et al. |
| 2006/0129004 A1 | 6/2006 | Lueken et al. |
| 2006/0161017 A1 | 7/2006 | Grass et al. |
| 2006/0183936 A1 | 8/2006 | Grass et al. |
| 2007/0117995 A1 | 5/2007 | Ortmann et al. |

FOREIGN PATENT DOCUMENTS

| | | |
|---|---|---|
| DE | 101 40 072 | 2/2003 |
| WO | 03 016320 | 2/2003 |
| WO | 03 016321 | 2/2003 |
| WO | 03 076448 | 9/2003 |
| WO | 03 078444 | 9/2003 |

OTHER PUBLICATIONS

U.S. Appl. No. 11/494,741, filed Jul. 28, 2006, Kaizik, et al.
U.S. Appl. No. 10/562,454, filed Aug. 18, 2006, Krissmann, et al.
U.S. Appl. No. 10/576,302, filed Apr. 19, 2006, Kaizik, et al.
U.S. Appl. No. 10/588.762, filed Aug. 8, 2006, Wiese, et al.
U.S. Appl. No. 10/584,492, filed Jun. 22, 2006, Ortmann, et al.
U.S. Appl. No. 09/708,646, filed Nov. 9, 2000, Hess, et al.
U.S. Appl. No. 10/584,492, filed Jun. 22, 2006, Ortmann, et al.
U.S. Appl. No. 10/505,879, filed Sep. 3, 2004, Borgmann.
U.S. Appl. No. 10/525,376, filed May 8, 2006, Moeller, et al.
U.S. Appl. No. 10/584,148, filed Jun. 22, 2006, Ortmann, et al.
U.S. Appl. No. 10/593,330, filed Sep. 19, 2006, Borgmann, et al.
U.S. Appl. No. 10/584,492, filed Jun. 22, 2006, Ortmann, et al.

* cited by examiner

METHOD FOR PRODUCING ORGANOACYLPHOSPHITES

The present invention relates to a process for preparing organoacyl phosphites and optionally organoacyl phosphonites and organoacyl phosphinites which have an organophosphite structural unit, by condensing phosphorus trihalides or organophosphorus halides with a compound which has a salicylic acid group and optionally further compounds bearing hydroxyl groups in the presence of polymeric basic ion exchange resins.

Owing to their broad field of application, organophosphorus compounds have gained considerable industrial importance. They are used, for example, as plasticizers, flame retardants, UV stabilizers and antioxidants. In addition, they constitute important intermediates in the preparation of fungicides, herbicides, insecticides and pharmaceuticals. Accordingly, a large number of preparative processes has been developed. Particularly important among the organophosphorus compounds is the substance class of organophosphites. One review of the preparative methods for organophosphites is by K. Sasse and can be found in "Methoden der Organischen Chemie" [Methods of Organic Chemistry] (Houben-Weyl), Volume XII/2, Chapter 1, Thieme Verlag, Stuttgart (1964) and L. Maier, G. Kosolapoff, "Organic Phosphorus Compounds", Volume 4, John Wiley & Sons, p. 255-462 and the literature references contained therein.

The preparation of triaryl phosphates by reacting phosphorus trihalides with suitable phenols succeeds in the presence of a catalyst in an inert solvent at temperatures of from 150 to 200° C. (DE 20 28 878, DE 20 07 070). The hydrogen chloride which is formed is distilled off in situ. This process has a series of disadvantages. In order to bring about the in situ distillation of the hydrogen chloride, high temperatures are necessary. Especially at elevated temperature, hydrogen chloride is extremely corrosive and therefore requires the use of special materials in the plant construction. In addition, the reaction times are very long, which has the consequence of a high fraction of by-products and therefore costly and inconvenient purification of the crude product.

It is therefore often industrially more advantageous to condense phosphorus trihalides, monoaryl dichlorophosphites or halodiaryl chlorophosphites with phenols in the presence of basic compounds which scavenge the hydrogen chloride being formed. The bases used are usually nitrogen compounds, for instance trialkylamines (DD 301615, U.S. Pat. No. 4,415,686, JP 54030140), dimethylformamide (JP 10053595, EP 511156), N,N-dialkylanilines or nitrogen heterocycles such as pyridine (G. Kosolapoff, "Organophosphorus Compounds", John Wiley & Sons (1950), p. 184). Other processes employ alkali metal and/or alkaline earth metal hydroxides (EP 0032202). JP 54030140 describes the condensation of phosphorus trihalides with phenols in the presence of substoichiometric amounts of amines, ammonium salts, carboxylic acids, guanidines, amides, amidines, sulfones and phosphines.

The document WO 91/09040 describes the preparation of sterically hindered triaryl phosphites starting from the corresponding phenols and phosphorus trihalide in the presence of mercaptothiazoles and dithiocarbamic acid derivatives.

WO 03/078444 describes the preparation of compounds having silyl groups as substituents, referred to as phosoxophites, by reacting suitable phosphorus-halogen compounds with a compound having an acid and an OH group in the presence of triethyalmine.

A review of the synthetic methods of organophosphites is given for example, in Houben-Weyl, "Methoden der Organischen Chemie", XII/1, p. 44 ff. A review of the methods for the synthesis of organophosphinites is given in Houben-Weyl, "Methoden der Organischen Chemie", XII/1, p. 210 ff.

One disadvantage of the known industrial processes is the removal of the base and/or its reaction products or the catalysts in the workup of the crude organophosphorus product. A distillative separation is often possible only with difficulty or even impossible as a consequence of the low vapor pressures of the components involved. When a solid base is used and/or the reaction products of the base occur in solid form or a precipitation of the base and/or its reaction products is possible, a removal from the crude product may be effected by filtration or sedimentation. On the industrial scale, especially in a continuous procedure, these separating operations are known to be extremely costly and inconvenient in the industrial construction and operation. They are sensitive toward changes in the operating parameters and/or type and properties of the substances to be separated. In general, it is also necessary to use large amounts of solvent, for example in order to wash product of value from the filtercake. However, this often succeeds only incompletely (U.S. Pat. No. 5,710,307).

When tertiary amines, especially triethylamine, are used, the trialkylammonium halides which precipitate out lead to a sharp increase in the viscosity of the reaction mixture and to the formation of wall deposits. Under these conditions, stirring and heat exchange are considerably complicated. In order to counter this disadvantage, the document EP 1 234 831 proposes relatively long-chain tertiary amines such as tri-n-propylamine, triisopropylamine, tri-n-butylamine, triisobutylamine and tri-tert-butylamine. Nevertheless, the fundamental disadvantages of filtration mentioned above remain on the industrial scale.

A further workup of the crude organophosphorus products may be effected by methods known to those skilled in the art, for example by (fractional) crystallization, sublimation, precipitation or chromatographic methods, in some cases also by distillation or rectification. The use of these separating methods on the industrial scale is also associated with a high level of technical complexity and expense.

The document EP 0 285 136 claims a process for purifying tertiary organophosphites to free them of pentavalent organophosphorus compounds which are by-produced in the synthesis or are formed as degradation or hydrolysis products of the tertiary organophosphites. The process envisages a treatment of the dissolved impure organophosphite with water at elevated temperature in the presence of a Lewis base. The Lewis bases used are inorganic salts (carbonates, hydroxides, oxides), tertiary amines and polymers which bear amine groups.

However, the synthesis of the organophosphorus compounds itself is not addressed. One disadvantage of the claimed process is in the treatment with water. Not only the impurities to be removed but also the tertiary organophosphites, especially (organo)chlorophosphites, themselves react under the given conditions, so that, depending on the hydrolysis stability of the organophosphites, a portion of the product of value is lost.

DE 100 53 272 describes the preparation of diphosphites in which one phosphite unit has a salicylic acid building block. DE 100 58 383 describes the preparation of phosphinines which have at least two phosphorus atoms. DE 101 14 868 describes the preparation of diphosphines. DE 101 40 083 and DE 101 40 072 describe the preparation of diphosphites in which both phosphite units have a salicylic acid building block. DE 101 400 86 describes the preparation of monophosphites which have a salicylic acid building block. DE 102 10 918 describes the preparation of diphosphites in which at least one phosphite likewise has a salicylic acid building block. All of the aforementioned documents describe the use of tertiary amines, especially of triethylamine, pyridine or N-methylpyrrolidinone, in the reaction of phosphorus halides with alcohols.

The existing processes have one or more of the following disadvantages:
a) The complete removal of the base used from the target product is costly and inconvenient.
b) The salts, formed in the reaction, of the bases used are frequently voluminous or occur in a particle size distribution which complicates the removal by filtration.
c) The maintenance of the desired reaction temperature is difficult owing to the high exothermicity.

It is therefore an object of the present invention to provide a simple process for preparing trivalent organophosphorus compounds which does not have one or more of these disadvantages.

It has been found that, surprisingly, this object can be achieved by preparing trivalent organic phosphorus compounds which have at least one P—O bond by reacting a trivalent phosphorus compound in which at least one halogen atom is bonded to the phosphorus atom with an organic compound which has at least one OH group in the presence of an ion exchange resin. Even though the base is present in heterogeneous phase, sufficient scavenging of the hydrogn halide released is surprisingly achieved.

The present invention therefore provides a process for preparing trivalent organophosphorus compounds which bear at least one structural unit S

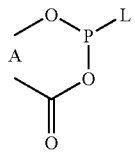

(S)

where A is a divalent substituted or unsubstituted alkyl or aryl radical which may form a ring system as per structural unit S, and the L radical is an organic radical bonded to the phosphorus atom via an oxygen or carbon atom, or is a halide, by condensing phosphorus compounds of the formula i $$PHal_aR_{(3-a)} \quad \text{(i)}$$

where Hal is halide selected from chloride, bromide and iodide, and the halides may be the same or different, R is an organic radical bonded to the phosphorus via a carbon or oxygen atom, and a=2 or 3, with an organic compound of the formula S'

(S')

where A is as defined for the structural unit S, which comprises carrying out the reaction in the presence of at least one basic ion exchange resin.

In particular, the present invention provides a process for preparing trivalent organophosphorus compounds which have at least one structural unit T

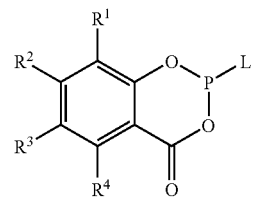

(T)

where $R^1$, $R^2$, $R^3$, and $R^4$ are each independently selected from monovalent substituted and unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms, H, F, Cl, Br, I, —$CF_3$, —$CH_2(CF_2)_jCF_3$ with j=0-9, —$OR^9$, —$COR^9$, —$CO_2R^9$, —$CO_2M$, —$SR^9$, —$SO_2R^9$, —$SOR^9$, —$SO_3R^9$, —$SO_3M$, —$SO_2NR^9R^{10}$, —$NR^9R^{10}$, —$N=CR^9R^{10}$, where $R^9$ and $R^{10}$ are each independently selected from H, monovalent substituted and unsubstituted aliphatic and aromatic hydrocarbon radicals having from 1 to 25 carbon atoms, and M is an alkali metal ion, formally half an alkaline earth metal ion, ammonium ion or phosphonium ion, or adjacent $R^1$ to $R^4$ radicals together form a fused substituted or unsubstituted aromatic, heteroaromatic, aliphatic, mixed aromatic-aliphatic or mixed heteroaromatic-aliphatic ring system; and the substituted hydrocarbon radicals may have as substituents those selected from —$N(R^5)_2$, —$NHR^5$, —$NH^2$, fluorine, chlorine, bromine, iodine, —OH, —CN, —C(O)—$R^5$, —C(O)H or —C(O)O—$R^5$, —$CF_3$, —O—$R^5$, —C(O)N—$R^5$, —OC(O)—$R^5$ and/or —$Si(R^5)_3$, where $R^5$ is a monovalent hydrocarbon radical preferably having from 1 to 20 carbon atoms, and, when a plurality of hydrocarbon radicals $R^5$ is present, they may be the same or different, and $R^1$, $R^2$, $R^3$ and $R^4$ radicals may be the same or different, and L is an organic radical bonded to the phosphorus atom via an oxygen or carbon atom, or is a halide, by condensing phosphorus compounds of the formula i $$PHal_aR_{(3-a)} \quad \text{(i)}$$

where Hal is halide selected from chlorine, bromine and iodine, and the halides may be the same or different, R is an organic radical bonded to the phosphorus via a carbon or oxygen atom and a=2 or 3, with an organic compound of the formula T'

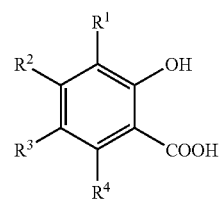

(T')

where the $R^1$ to $R^4$ radicals are each as defined for the structural unit T, which comprises carrrying out the reaction in the presence of at least one basic ion exchange resin.

The process according to the invention has the following advantages over the conventional processes:
a) There are no saltlike by-products which can only be removed with difficulty from the target product.

b) The base used is in solid form and, despite reaction with the hydrogen halide, does not change its state of matter and substantially retains its size. The ion exchanger of the process according to the invention, typically present as a packing or beads, can be removed from the reaction mixture by the simplest means, for example by using coarse-mesh sieves adapted to the size of the ion exchanger particles.

c) Adhesion of large amounts of product of value is prevented by the size and shape of the ion exchanger alone. The use of packings or particles of relatively large particle size makes the surface of the ion exchanger small relative to the volume compared to a precipitated base of the conventional type. Therefore, it is also only necessary to use small amounts of solvent in the process according to the invention in order to flush any adhering product of value off the surface of the consumed base.

d) When ion exchanger is used, the rate constant of the reaction is lower than when homogeneously dissolved bases are used. As a result, the exothermic reaction becomes easy to control.

e) during the reaction, no voluminous salts which, as a consequence of the rise in viscosity that they bring about, could cause concentration and temperature differences in the reaction mixture are formed.

The process according to the invention is described by way of example herein below without the invention being restricted to these embodiments. Further variants which likewise form part of the subject matter of the present invention and whose field of application is evident from the description and the claims are evident to those skilled in the art.

In the process according to the invention for preparing trivalent organophosphorus compounds which bear at least one structural unit S

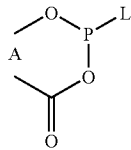

(S)

where A is a divalent substituted or unsubstituted alkyl or aryl radical which may form a ring system as per structural unit S, and the L radical is an organic radical bonded to the phosphorus atom via an oxygen or carbon atom, or is a halide, by condensing phosphorus compounds of the formula i $PHal_aR_{(3-a)}$ (i)

where Hal is halide selected from chlorine, bromine and iodine, and the halides may be the same or different, R is an organic radical bonded to the phosphorus via a carbon or oxygen atom, and a=2 or 3, with an organic compound of the formula S'

(S')

where A is as defined for the structural unit S, the reaction is carried out in the presence of at least one basic ion exchange resin, preferably an ion exchange resin present in the form of the free amines (i.e. not present in the OH form).

When the A radical is an aryl radical, it is preferably bonded to the radical of the structural unit S via two adjacent bonds (for example 1,2-aryl or 2,3-aryl), in such a way that the structural unit S has a ring having 6 atoms (a phosphorus atom, 2 oxygen atoms and 3 carbon atoms). When the divalent A radical of the structural unit S is an alkyl radical, it has, in the chain which is joined to the structural unit at both ends, preferably from 1 to 3, more preferably 1 or 2, carbon atoms. The A radical may have further carbon atoms, preferably from 1 to 20 carbon atoms, which are bonded to the carbon atom or atoms of the chain in the case of an alkyl radical or to the carbon atoms of the aryl radical which are not joined to the sturctural unit S. In addition to pure hydrocarbon radicals as substituents, the A radicals may also have further substituents, with the proviso that the substituents do not influence the properties, especially with regard to the effectiveness as a ligand. Possible substituents may be selected, for example, from the halogens, nitro, cyano, alkoxy, ether and alcohol groups. Typical A radicals may be, for example, —CH$_2$—, —CH$_2$CH$_2$—, —CH$_2$CH$_2$CH$_2$—, 1,2-phenylene (—C$_6$H$_4$—), 1,2-naphthylene (—C$_{10}$H$_6$—), 2,3-naphthylene, 3,5-dichloro-1,2-phenylene, 3,5-dibromo-1,2-phenylene, 3-iodo-5-methyl-1,2-phenylene, 3,5-diisopropyl-1,2-phenylene, 3,5,6-trichloro-1,2-phenylene, 3-phenyl-1,2-phenylene, 1,1-diethyl-1,1-methylene, 1,1-cyclohexylidene, 1,1-cycloheptylidene, 3-isopropyl-6-methyl-1,2-phenylene and similar radicals. The A radical is preferably selected from 1,1-alkylene, 1,2-alkylene, 1,2-phenylene, 1,2-naphthylene and 2,3-naphthylene as divalent radicals or substituted derivatives thereof, in particular halogen- or alkyl-substituted derivatives.

The process according to the invention is particularly suitable for preparing trivalent organophosphorus compounds which have at least one structrual unit T

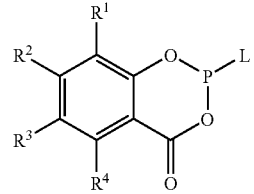

(T)

where $R^1$, $R^2$, $R^3$, and $R^4$ are each independently selected from monovalent substituted and unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms, H, F, Cl, Br, I, —CF$_3$, —CH$_2$(CF$_2$)$_j$CF$_3$ with j=0-9, —OR$^9$, —COR$^9$, —CO$_2$R$^9$, —CO$_2$M, —SR$^9$, —SO$_2$R$^9$, —SOR$^9$, —SO$_3$R$^9$, —SO$_3$M, —SO$_2$NR$^9$R$^{10}$, —NR$^9$R$^{10}$, —N=CR$^9$R$^{10}$, —SiR$^9$R$^{10}$R$^{11}$ where R$^9$ and R$^{10}$ are each independently selected from H, monovalent substituted and unsubstituted aliphatic and aromatic hydrocarbon radicals having from 1 to 25 carbon atoms, and M is an alkali metal ion, formally half an alkaline earth metal ion, ammonium ion or phosphonium ion, or adjacent R$^1$ to R$^4$ radicals together form a fused substituted or unsubstituted aromatic, heteroaromatic, aliphatic, mixed aromatic-aliphatic or mixed heteroaromatic-aliphatic ring system; and the substituted hydrocarbon radicals may have as substituents those selected from —N(R$^5$)$_2$, —NHR$^5$, —NH$_2$, fluorine, chlorine, bromine, iodine, —OH, —CN, —C(O)—R$^5$, —C(O)H or —C(O)O—R$^5$, —CF$_3$, —O—R$^5$, —C(O)N—R$^5$, —OC(O)—R$^5$ and/or —Si(R$^5$)$_3$, where R$^5$ is a monovalent hydrocarbon radical preferably having from 1 to 20 carbon atoms, for example an alkyl radical, in particular methyl, ethyl, propyl or tert-butyl radical, a cycloalkyl radical, in particular cyclopentyl or cyclhexyl radical, or an aryl radical, in particular phenyl or naphthyl radical, and, when a plurality of hydrocarbon radicals R$^5$ is present, they may be the same or different, and R$^1$, R$^2$, R$^3$ and R$^4$ radicals may be the same or different, and L is an organic radical bonded to the phosphorus atom via an oxygen or carbon atom, or is a halide, by condensing phosphorus compounds of the formula i

$$PHal_a R_{(3-a)} \tag{i}$$

where Hal is halide selected from chlorine, bromine and iodine, and the halides may be the same or different, R is an organic radical bonded to the phosphorus via a carbon or oxygen atom and a=2 or 3, with an organic compound of the formula T'

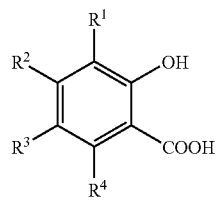

(T')

where the R$^1$ to R$^4$ radicals are each as defined for the structural unit T.

The process according to the invention will be described hereinbelow usually, by way of example, with reference to compounds which have the structural element T as a specific form of the structural element S without the invention being restricted to the structural element T.

The halide Hal in the phosphorus compounds i is preferably chlorine. The R$^1$ and R$^2$, R$^2$ and R$^3$, or R$^3$ and R$^4$ radicals may in particular be benzofused. Nonbenzofused R$^1$ to R$^4$ radicals may in particular be primary, secondary or tertiary alkyl groups such as methyl, ethyl, n-propyl, isopropyl, n-butyl, isobutyl, t-butyl, amyl, sec-amyl, t-amyl, 2-ethylhexyl, iso-nonyl, alicyclic groups such as cyclohexyl, methylcyclohexyl or cyclooctyl, or aromatic groups such as phenyl, naphthyl, tolyl or xylyl. The organic R or L radical may in particular be a W radical which may be a substituted or unsubstituted aliphatic, alicyclic, aliphatic-alicyclic, heterocyclic, aliphatic-heterocyclic, aromatic-aromatic or aliphatic-aromatic hydrocarbon radical having from 1 to 50 carbon atoms, and the substituted hydrocarbon radicals may have as substituents those selected from —N(R$^5$)$_2$, —NHR$^5$, —NH$_2$, fluorine, chlorine, bromine, iodine, —OH, —CN, —C(O)—R$^5$, —C(O)H or —C(O)O—R$^5$, —CF$_3$, —O—R$^5$, —C(O)N—R$^5$, —OC(O)—R$^5$ and/or —Si(R$^5$)$_3$, where R$^5$ is a monovalent hydrocarbon radical preferably having from 1 to 20 carbon atoms, and, when a plurality of hydrocarbon radicals R$^5$ is present, they may be the same or different, or is an organic radical as defined for the W radical which has at least one substituted or unsubstituted phosphite, phosphonite, phosphinite and/or acylphospite radical, and substituents may be selected from those defined for the W radical. The substituents are preferably restricted to those which have no influence on the reaction itself. Particularly preferred substituents for the organic R or L radicals may be selected from the halogens, for example chlorine, bromine and iodine, the alkyl radicals, for example methyl, ethyl, propyl, isopropyl, butyl, sec-butyl, t-butyl, neopentyl, sec-amyl, t-amyl, isooctyl, t-octyl, 2-ethylhexyl, isononyl, isodecyl and octadecyl, the aryl radicals, for example phenyl, naphthyl and anthracyl, the alkylaryl radicals, for example tolyl, xylyl, dimethylphenyl, diethylphenyl, trimethylphenyl, triethylphenyl and p-alkylphenyl, the aralkyl radicals, for example benzyl and phenylethyl, the alicyclic radicals, for example cyclopentyl, cyclohexyl, cyclooctyl, cyclohexylethyl and 1-methylcyclohexyl, the alkoxy radicals, for example methoxy, ethoxy, propoxy, butoxy and pentoxy, the aryloxy radicals, for example phenoxy and naphthoxy, —OC(O)R$^5$ or —C(O)R$^5$, where R5 is a monovalent hydrocarbon radical, for example acetyl, propionyl, trimethylacetoxy, triethylacetoxy and triphenylacetoxy, and the silyl radicals —Si(R)$_3$ having three hydrocarbon radicals, for example trimethylsilyl, triethylsilyl or triphenylsilyl.

When the compounds used in the process according to the invention have amine groups, i.e. —NH$_2$, —N(R$^5$)$_2$ or —N(alkyl)$_2$ or —NH(alkyl) or —NHR$^5$, they have to function as a weaker base relative to the amine groups of the ion exchanger in equilibrium reactions. Compounds which have amine groups and cannot fulfill this condition cannot be used (directly) as reactants in the process according to the invention. One possibility of still using such compounds is to protect the appropriate groups by the incorporation of protective groups in a known manner, and, after carrying out the process according to the invention, remove the protective group again.

The trivalent organophosphorus compounds prepared by means of the process according to the invention may preferably be those which are selected from the compounds of the following formulae

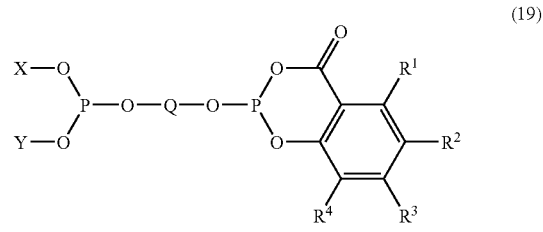

(19)

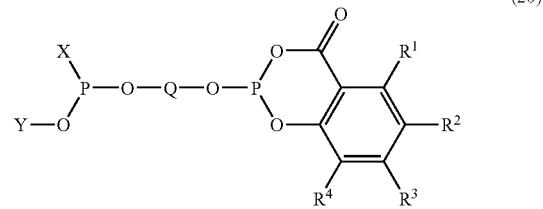

(20)

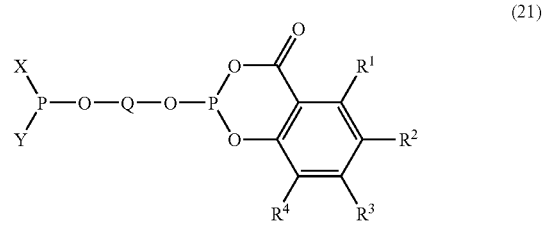

(21)

where X and Y are each substituted or unsubstituted, aliphatic, alicyclic, aliphatic-alicyclic, heterocyclic, aliphatic-heterocyclic, aromatic-aromatic or aliphatic-aromatic hydrocarbon radicals having from 1 to 50 carbon atoms, where X and Y are the same or different or covalently joined together, and where Q is an at least divalent, substituted or unsubstituted, aliphatic, alicyclic, aliphatic-alicyclic, heterocyclic, aliphatic-heterocyclic, aromatic, aromatic-aromatic or aliphatic-aromatic hydrocarbon radical, and the substituted hydrocarbon radicals may contain as substituents those selected from —N($R^5$)$_2$, —NH$R^5$, —NH$_2$, fluorine, chlorine, bromine, iodine, —OH, —CN, —C(O)—$R^5$, —C(O)H or —C(O)O—$R^5$, —CF$_3$, —O—$R^5$, —C(O)N—$R^5$, —OC(O)—$R^5$ and/or —Si($R^5$)$_3$, where $R^5$ is a monovalent hydrocarbon radical preferably having from 1 to 20 carbon atoms, and, when a plurality of hydrocarbon radicals $R^5$ is present, they may be the same or different, and where $R^1$ to $R^4$ may each be as defined above. The substituents are preferably restricted to those which have no influence on the reaction itself. Particularly preferred substituents may be selected from the preferred substituents specified for R and L.

The trivalent organophosphorus compounds prepared by the process according to the invention may equally possibly be phosphites of the formula 10 or 11

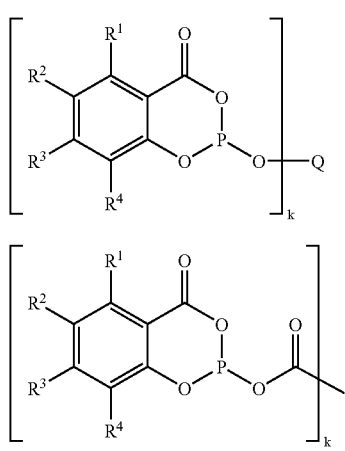

(10)

(11)

where $R^1$, $R^2$, $R^3$, and $R^4$ are each as defined above, Q is a k-valent substituted or unsubstituted, aliphatic, alicyclic, mixed aliphatic-alicyclic, heterocyclic, mixed aliphatic-heterocyclic, aromatic, heteroaromatic, mixed aliphatic-aromatic hydrocarbon radical having from 1 to 50 carbon atoms, and aliphatic moieties of Q may contain oxygen, sulfur and/or nitrogen, and the substituted hydrocarbon radicals may have as substituents those selected from —N($R^5$)$_2$, —NH$R^5$, —NH$_2$, fluorine, chlorine, bromine, iodine, —OH, —CN, —C(O)—$R^5$, —C(O)H or —C(O)O—$R^5$, —CF$_3$, —O—$R^5$, —C(O)N—$R^5$, —OC(O)—$R^5$ and/or —Si($R^5$)$_3$, where $R^5$ is a monovalent hydrocarbon radical preferably having from 1 to 20 carbon atoms, and, when a plurality of hydrocarbon radicals $R^5$ is present, they may be the same or different, k is at least 2, and $R^1$, $R^2$, $R^3$ and $R^4$ in the individual structural elements T bonded to Q may in each case be defined identically or differently. The substituents are preferably restricted to those which have no influence on the reaction itself. Particularly preferred substituents may be selected from the preferred substituents specified for R and L.

It is equally possible by the process according to the invention to prepare the compounds described in WO 03/078444 and referred to as phosoxophites.

Bisphosphites of the structure 19 are preferably prepared by condensing at least di-OH-substituted hydrocarbons Q' where Q' is a substituted or unsubstituted aliphatic, alicyclic, mixed aliphatic-alicyclic, heterocyclic, mixed aliphatic-heterocyclic, aromatic, heteroaromatic, mixed aliphatic-aromatic hydrocarbon having from 1 to 50 carbon atoms, and aliphatic moieties of Q' may contain oxygen, sulfur and/or nitrogen, and the substituted hydrocarbons may have as substituents those selected from —N($R^5$)$_2$, —NH$R^5$, —NH$_2$, fluorine, chlorine, bromine, iodine, —OH, —CN, —C(O)—$R^5$, —C(O)H or —C(O)O—$R^5$, —CF$_3$, —O—$R^5$, —C(O)N—$R^5$, —OC(O)—$R^5$ and/or —Si($R^5$)$_3$, where $R^5$ is a monovalent hydrocarbon radical preferably having from 1 to 20 carbon atoms, and, when a plurality of hydrocarbon radicals $R^5$ is present, they may be the same or different, with diorganohalophosphites 2 and salicylic phosphorus halide derivatives T where L=Hal in the presence of one or more basic ion exchange resins. The substituents are preferably restricted to those which have no influence on the reaction itself. Particularly preferred substituents for Q' may be selected from the preferred substituents specified for R and L.

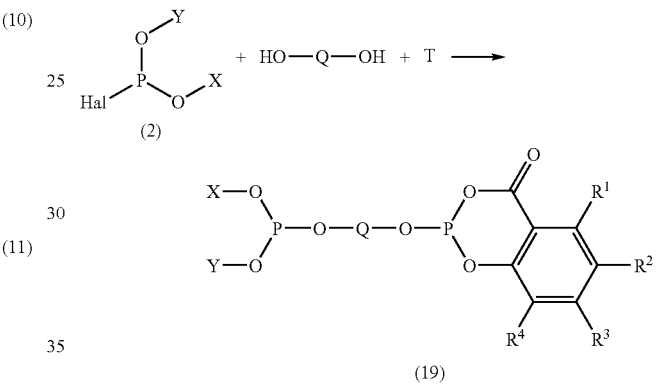

(2)

(19)

Phosphite-phosphonite compounds of the structure 20 are prepared by means of the process according to the invention preferably by condensing di-OH-substituted hydrocarbons Q' with haloorganophosphonites 4 and salicylic phosphorus halide derivatives T where L=Hal in the presence of one of more basic ion exchange resins.

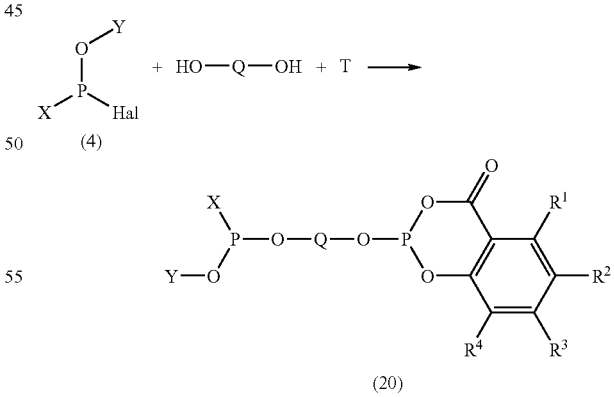

(4)

(20)

Phosphite-phosphinite compounds of the structure 21 are prepared by means of the process according to the invention preferably by condensing di-OH-substituted hydrocarbons Q' with haloorganophosphinites 9 and salicylic phosphorus halide derivatives T where L=Hal in the presence of one or more basic ion exchange resins.

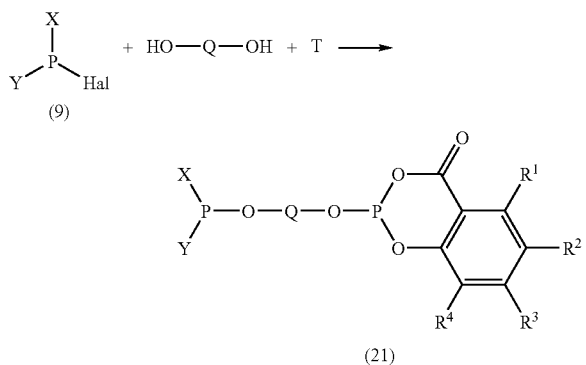

In the formulae 19 to 21, X and Y may each be as defined above. The hydrocarbons Q' have at least two OH groups. The hydrocarbons Q' having two OH groups are preferably compounds selected from the substituted or unsubstituted compounds 1,4-dihydroxybenzene, 1,2-dihydroxybenzene, 1,8-dihydroxynaphthalene, 1,1'-binaphthyl-2,2'-diol or 2,2'-binaphtyl-1,1'-diol.

The phosphorus compound of the formula i used is preferably at least one compound selected from the compounds of the following formulae:

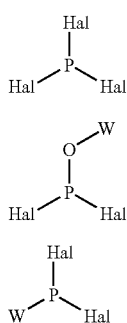

where W is an organic radical as defined above. The phosphorus compound of the formula i used may in particular be a compound of the formula 1 which is prepared by reacting a compound 0 with an organic compound W' having at least one hydroxyl group, preferably likewise in the presence of a basic ion exchanger. The compounds W' having at least one hydroxyl group used may be a substituted or unsubstituted compound having an OH group, for example selected from methanol, ethanol, n-propanol, iso-propanol, 1-butanol, 2-butanol, t-butanol, 2-ethylhexanol, isononanol, isodecanol, isotridecanol, phenol, phenol derivatives, or compounds Q' having two or more OH groups, for example selected from 1,4-dihydroxybenzene, 1,2-dihydroxybenzene, 1,8-dihydroxynaphthalene, 1,1'-binaphtyl-2,2'-diol, 2,2'-binaphtyl-1,1'-diol, di- or polyols, for example glycol or sugars, for example cyclodextrins, or the compounds denoted by formula VII in WO 03/078444 or compounds having two or more carboxylic acid groups or a compound which has one or more OH groups and may have one or more of the structural units T, and the substituted compounds may have substituents selected from primary, secondary and tertiary alkyl groups, alicyclic groups, aromatic groups, $-N(R^5)_2$, $-NHR_5$, $-NH_2$, fluorine, chlorine, bromine, iodine, $-CN$, $-C(O)-R^5$, $-C(O)H$ or $-C(O)O-R^5$, $-CF_3$, $-O-R^5$, $-C(O)N-R^5$, $-OC(O)-R^5$ and/or $-Si(R^5)_3$, where $R^5$ is a monovalent hydrocarbon radical preferably having from 1 to 20 carbon atoms, and, when a plurality of hydrocarbon radicals $R^5$ is present, they be the same or different. The substituents are in turn restricted to those which have no influence on the reaction itself. Particularly preferred substituents may be selected from the preferred substituents specified for R and L.

It may be particularly advantageous when the compound having at least one hydroxyl group used is a compound which originally has at least two hydroxyl groups and is obtained by reacting at least one of these groups with a compound of the formula 0 and a compound of the formula T' or an aromatic compound which has two adjacent hydroxyl groups on the aromatic ring. In this way, the compounds of the formulae 10 and 11 and also specific compounds of the formula 19 in which X and Y are joined covalently (in an aromatic ring system) in particular are obtainable.

To prepare compounds of the formula 1, preference is given in each case to initially charging the phosphorus compound together with one or more basic ion exchange resins and subsequently metering in the compound having at least one OH group. It is also possible to initially charge the compound having an OH group together with the ion exchanger and add the phosphorus compound dropwise.

In the preparation of asymmetric diphosphorus compounds of the formula 10, 11, 19, 20, and 21 it has been found to be advantageous when the compound having OH groups is initially charged together with one or more basic ion exchange resins and one or more phosphorus compounds are subsequently metered in.

In the preparation of symmetric diphosphorus compounds of the formulae 10 and 11, either the compound having OH groups or the phosphorus compound may be initially charged together with the ion exchanger and the other compound accordingly metered in.

To prepare the compounds 19, 20 and 21, it may be advantageous when a compound selected from the compounds of the following formulae

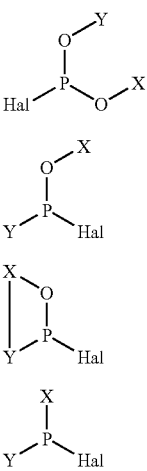

where Hal is halide, Y and X are substituted or unsubstituted, aliphatic, alicyclic, aliphatic-alicyclic, heterocyclic, aliphatic-heterocyclic, aromatic-aromatic or aliphatic-aromatic, hydrocarbon radicals having from 1 to 50 carbon atoms, and X and Y may be the same or different or be covalently joined together, is reacted with a compound Q' having at least two hydroxyl groups, preferably in the presence of a basic ion exchanger. The substituted hydrocarbons may have one or more substituents selected from primary, secondary and tertiary alkyl groups, alicyclic groups, aromatic groups, —N(R$^5$)$_2$, —NHR$^5$, —NH$_2$, fluorine, chlorine, bromine, iodine, —CN, —C(O)—R$^5$, —C(O)H or —C(O)O—R$^5$, —CF$_3$, —O—R$^5$, —C(O)N—R$^5$, —OC(O)—R$^5$ and/or —Si(R$^5$)$_3$, where R$^5$ is a monovalent hydrocarbon radical having preferably from 1 to 20 carbon atoms, and, when a plurality of hydrocarbon radicals R$^5$ is present, they may be the same or different. The substituents are in turn preferably restricted to those which have no influence on the reaction itself. Particularly preferred substituents for X and Y may be selected from the preferred substituents specified for R and L. The product which is obtained from this reaction and has at least one hydroxyl group is either reacted directly with a compound which has the structural unit T (specific type of the compound S) in which L is Hal, or initially with a compound 0 and subsequently with a compound T'. Preference is given to carrying out all of these reactions in the process according to the invention in the presence of a basic ion exchanger.

According to K. Sasse in "Methoden der Organischen Chemie" (Houben-Weyl), Volume XII/2, Chapter 1, p. 62 ff., Thieme Verlag, Stuttgart (1964) and G. M. Kosolapoff, "Organophosphorus Compounds", chap. 7, XV, pp. 139, John Wiley, New York (1950) and the literature references contained therein, the preparation of asymmetric organophosphites and asymmetric phosphonites succeeds by stepwise reaction of the organophosphorus halides or phosphorus halides used as starting substances with compounds containing hydroxyl groups in the presence of amines. Depending on the desired target compound, the process according to the invention may comprise one or more reaction steps, and the reaction of in each case one phosphorus-halogen bond with one hydroxyl group is one reaction step. Accordingly, the process according to the invention may be performed as a multistage process for preparing asymmetric organophosphites and asymmetric phosphonites, in which case the reaction steps are each carried out in the presence of a (weakly) basic ion exchanger. The generally possible reaction steps are detailed in the following reaction schemes:

As illustrated in the formulae ii, iii and iv, it is possible, starting from a phosphorus trihalide, by reacting with one equivalent of a compound containing one hydroxyl group HO—W, to prepare an organophosphorus dihalide, by reacting the organophosphorus dihalide with a further equivalent of a compound containing one hydroxyl group HO—X, to prepare a diorganophosphorus halide, and, by reacting further with one equivalent of a compound containing one hydroxyl group HO—Y, to finally prepare an asymmetric triorganophosphite. In the preparation of asymmetric phosphonites, an analogous procedure according to the formulae v and vi may be employed.

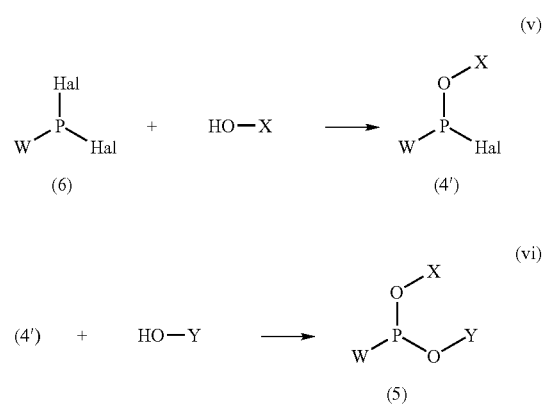

In the following formulae vii and viii, the inventive stepwise preparation of a diphosphorus compound which has a structural unit S (the special case of the structural unit T is illustrated by way of example) is shown using the example of a bisphosphite 10. A dihydroxyl compound 22 is reacted with one equivalent of a halodiorganophosphite 2 to give the compound 23 which is finally reacted with a comppound 17 which has the structural unit S or T to give the bisphosphite 10. The halodiorganophosphites mentioned may be the same or different, so that symmetric or asymmetric bisphosphites are obtained.

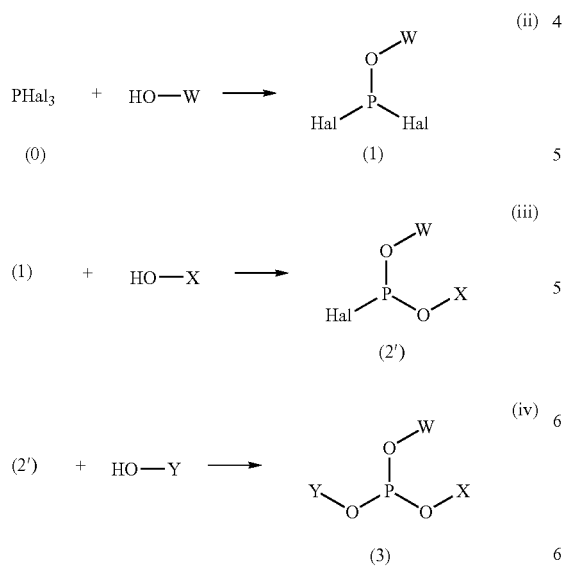

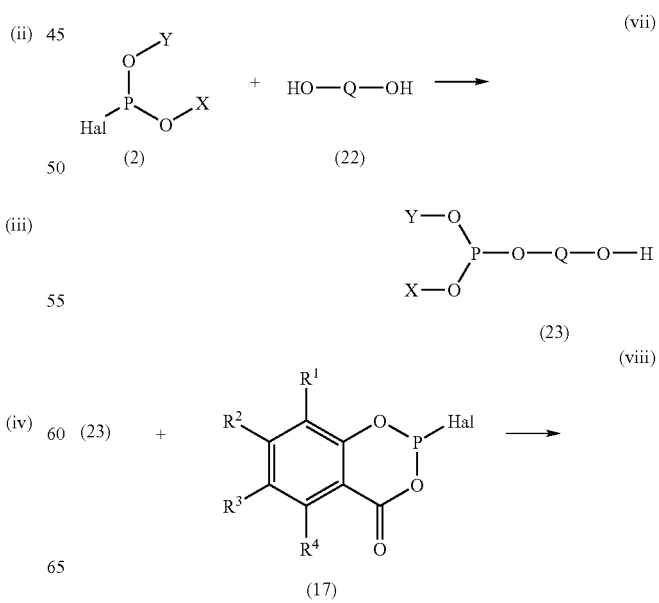

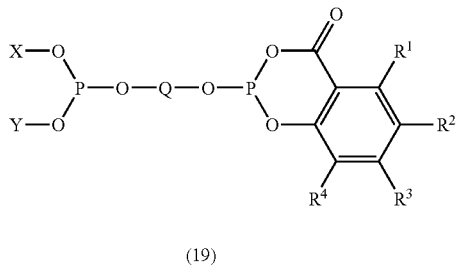

(19)

In the formulae ii to viii, X, Y and Q are each as defined above.

According to the formula vii, dihydroxyl compounds 22 may be reacted with diorganophosphites 2, halodiorganophosphonites 4 or 7, haloorganophosphinites 9. In the second reaction step viii, the compounds obtained by vii may be reacted with a compound having the structural unit S or T. In two reaction steps, asymmetric diphosphorus compounds of the formulae 19, 20 and 21 may thus be prepared. The compound 17 used in step viii (bicyclic phosphochloridite) may be obtained by reacting (condensing) the compound S' or T' (a 2-hydroxybenzoic acid derivative) with a compound 0. By directly reacting k equivalents of the compound 17 with one equivalent of a compound Q', it is possible to prepare compounds of the formula 10 or 11 where k is the number of OH groups in the compound Q', and, to prepare the compound 11, the compound Q' has a number k of acid groups. Preference is given in turn to carrying out all reactions steps in the presence of a basic ion exchanger.

In the case of the same organophosphorus halides, the preparation of the symmetric diphosphorus compounds, for example specific compounds of the formulae 10 and 11, may of course be effected in one process step. When the reactivities of the two organophosphorus halides toward dihydroxyl compounds 22 are sufficiently different, the preparation of asymmetric diphosphorus compounds may likewise be carried out in one process step. Otherwise, one process step has to be provided for each reaction step.

In a similar manner to the reactions vii and viii, compounds which bear more than two phosphorus units may be prepared by reacting compounds which have three or more hydroxyl groups stepwise with organophosphorus halides.

When a compound which still contains one or more hydroxyl groups, for example a compound of the structure 24

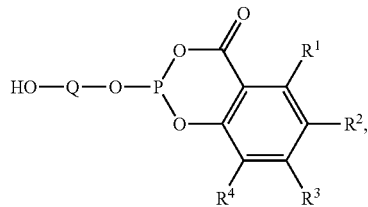

(24)

is the target of the preparation, the reaction sequence may be terminated at this stage after the reaction of a compound of the formula 17 with a compound of the formula 22. Complete conversion of the hydroxyl groups is not necessary.

The reaction steps illustrated in reaction schemes ii to viii may be carried out batchwise. In this case, one coupling component is initially charged together with one or more ion exchange resins and the second coupling component is subsequently metered in. The feed of the components or feed of solvent may be used in some cases to control the heat production rate or the temperature in the reaction mixture. In the batchwise method, it is important for a very high yield of desired product to initially charge and meter in the correct coupling component. For example, in the case of the selective preparation of asymmetric organophosphorus compounds of the formulae 1, 2, 3, 4, 5 or 6 according to schemes ii to vi, preference is given to initially charging the phosphorus compound, i.e. the phosphorus halide or the organophosphorus halide together with one or more basic ion exchange resins and subsequently metering in the compound having an OH group (hydroxyl component). In the case of the selective preparation of asymmetric diphosphorus compounds according to schemes vii and viii, preference is given to initially charging the component having OH groups together with one or more ion exchange resins and subsequently metering in the organophosphorus halides.

After each process step, but also after each reaction step, the crude product may be worked up and reacted further in the next reaction step. However, it may also be more advantageous, after the complete conversion of one coupling component, to directly add the next component and to dispense with the workup between the two reaction steps. In the context of the present invention, the reaction of in each case one phosphorus-halogen bond with one hydroxyl group should be regarded as one reaction step.

The reaction time in the individual reaction steps may be the same or different, but in each case sufficiently long in order to achieve the desired conversion. The reaction temperatures in the individual reaction steps may be the same or different. The basic ion exchange resin or resins used in the individual reaction steps may be the same or different.

The reactors used for batchwise reaction control may be stirred tanks. The basic ion exchange resin or resins may be used in the reaction mixture as freely mobile beads. It is also possible to combine the ion exchange resin or resins in the form of packages to which the convection stream of the stirrer flows. It is likewise possible to use spinning basket stirrers. In addition, the reactor systems used may be stirred reactors having full recycling (loop reactors). The flow to the ion exchange resin bed may be from above or below.

In another preferred embodiment of the process according to the invention, the reaction steps shown in the schemes ii to viii may also be carried out continuously in reaction spaces connected in series. Such a reaction sequence is illustrated in FIG. 1: The reactant A and the first coupling component K1 are conducted into a first reaction stage I. The effluent of the first reaction stage B is subsequently, like a second coupling component K2 too, conducted into a second reaction stage II. It is also possible that the coupling components K mentioned are effluents of one continuous, or of a plurality of continuous, reactors which are optionally connected in series, i.e. are reactor sequences of the type outlined in FIG. 2 in parallel and converging connection.

In order to achieve a very high yield of the desired product in the preparation of asymmetric products, the concentration ratio of the reactants is to be appropriately set in each stage by the ratios of the particular feeds. Typically, equimolar or approximately equimolar amounts are set. In the preparation of symmetric diphosphites which have an acylphosphite unit (T) or a structural unit S, it has been found to be advantageous when the molar ratio of acylphosphorus halide compound to dihydroxy compound is set to from 1:1 to 1.2:1.

The residence time of the reactants in the individual reaction steps may also be the same or different in the continuous mode, but in each case sufficient in order to achieve the desired conversion in the particular stage. The basic ion exchange resin or resins used in the individual reaction steps may be the same or different.

The reactors used for continuous reaction control may be continuous stirred tanks. The basic ion exchange resin or resins may be used in the reaction mixture as freely mobile beads. It is also possible to combine the ion exchange resin or resins in the form of packages to which the convection stream of the stirrer flows. It is likewise possible to use spinning basket stirrers. In addition, tubular reactors may be used. The flow to the ion exchange resin bed may be from above or below. In the continuous reactors, partial recycling of the reactor effluents may be advantageous. In the case of the arrangement of continuous reactors in a reactor battery, the recycled fraction of the effluent of one reaction stage may be partly or fully recycled into the same stage, partly or fully conducted to the start of the preceding stage or partly or fully conducted to the start of the first stage of the first reactor of the reactor battery.

Quite generally, and irrespective of whether the process is carried out continuously or batchwise, when a plurality of reaction steps is carried out, identical or different ion exchangers may be used in the reaction steps. Equally, when a plurality of reaction steps is carried out, identical or different temperatures may be set in the reaction steps. The temperature selected in the reaction stages depends substantially upon the reactivity of the feedstocks and may, within a sequence of reactors, be the same or different. The temperature is preferably increased within a reactor battery. The reaction temperatures are preferably from −50° C. to 150° C., preferably from −10° C. to 120° C. and more preferably from 20° C. to 100° C. As already described, the temperature may be controlled by the feed control of the components. It is equally possible to keep the temperature at a certain temperature by the use of heatable/coolable reactors. It is also possible to combine both measures for temperature regulation. In this way, quasi-isothermal operation of the entire process or of individual process or reaction steps is possible, which makes possible particularly exact setting to the optimum reaction temperature which can lead to better yields.

The process according to the invention is preferably carried out in the presence of a solvent or of a plurality of solvents. The selection of the solvent depends upon the solubility of the feedstocks. In addition, the solvent has to be substantially inert toward the feedstocks under the reaction conditions. The solvent may also be added to the reaction mixture to control the temperature. Preference is given to using solvents which may function as proton carriers.

Preferred solvents are, for example, aromatics such as benzene, chlorobenzene, toluene or xylenes, open-chain or cyclic alkanes such as pentane, n-hexane, n-heptane, cyclohexane or methylcyclohexane, open-chain or cyclic ethers such as diethyl ether, diisopropyl ether, methyl tert-butyl ether, anisole, tetrahydrofuran, 1,4-dioxane, 1,3-dioxolane, esters such as ethyl acetate, isobutyl acetate, tert-butyl acetate, cyclic carbonic esters such as ethylene carbonate, propylene carbonate and 1,2-butylene carbonate, ketones such as acetone, 2-butanone, 3,3-dimethyl-2-butanone, aromatic and aliphatic nitriles such as benzonitrile, propionitrile and acetonitrile, lactones, pyrrolidones, e.g. N-methylpyrrolidone, formamides, e.g. dimethylformamide, sulfoxides, e.g. dimethyl sulfoxide, and also N-alkylmorpholines, pyridines, quinolines, nitrogen bases such as amines and sulfolane. It is of course also possible to use mixtures of these solvents.

A particularly preferred embodiment of the process according to the invention is carried out in the presence of a proton transferrer which is preferably present in homogeneous form in the reaction mixture or reaction solution. The proton transferrers used may be bases which are weaker bases than the weakly basic ion exchangers. The proton transferrers used are preferably those compounds which, in addition to the function as a proton transferrer, may also assume the function of the solvent. Such compounds may be, for example, N-methylpyrrolidone or methylimidazole. The use of a proton transferrer which is homogeneously distributed in the reaction mixture may increase the reaction rate, since the reaction is promoted by the reactants no longer having to come into contact directly with the ion exchanger, but rather only with the weaker base which is, though, homogeneously distributed in the reaction mixture. The proton transferrer then reacts further with the ion exchanger, but serves only as a transferrer. In the reaction mixture, there is preferably a molar ratio of proton transferrer to the free base provided by the ion exchanger of from 0.0001:1 to 1:1, preferably from 0.001 to 0.01.

Preference is given to carrying out the process according to the invention in the presence of one or more polymeric, (weakly) basic ion exchange resins, preferably based on styrene-divinylbenzene copolymers, in order to scavenge the hydrogen halide formed in the condensation of phosphorus trihalides or organophosphorus halides with organic compounds bearing hydroxyl groups. Particular preference is given to using ion exchange resins based on styrene-divinylbenzene copolymers which bear N,N-dialkylamine groups, for example N,N-dimethylamino groups. It is possible to use macroreticular ion exchange resins or those of the gel type. Particular preference is given to using macroreticular ion exchange resins.

Very suitable for use in the process according to the invention are commercially available (weakly) basic ion exchange resins, for example Lewatit MP62, DOWEX M-43 or Amberlyst A21.

Preference is given to using the ion exchanger in the form of particles, preferably having an average particle size of from 10 μm to 2 mm, more preferably from 0.1 to 1.5 mm, or in the form of a fixed package. In this way, it is ensured that the ion exchanger can be very simply removed from the reaction mixture or separated from it.

In the process according to the invention, at least sufficient (weakly) basic ion exchanger is used that for each mole of acid which is released in the compound formation or formations, at least one mole of free base is available on the ion exchanger. Preference is given to using sufficient ion exchanger that the ratio of moles of acid resulting from the release to moles of free base released by the ion exchanger is from 1:1 to 3:1, preferably from 1.1:1 to 2:1.

Before it is used in the process according to the invention, the ion exchange resin is preferably dried by known techniques, for example by heat treatment under reduced pressure (G. Mohorcic, M. Pregelj, M. Pirs, Ion Exchange and Membranes (1975), 2(2), 107-110, C. Buttersack, K. Struss, H. Widdecke, J. Klein, Reactive Polymers, Ion Exchangers, Sorbents (1987), 5(2), 171-180) or by azeotropic distillation with suitable azeotroping agents (GB 1120402).

To carry out the process in continuous or quasi-continuous mode, at least two parallel reactors are provided per reaction step or process step and are connected in such a way that when the ion exchanger is exchanged, regenerated or dried in one of the reactors, the reaction can be continued in the other reactor.

In order to the keep the costs of the process low, it is appropriate to regenerate the ion exchange resin laden with hydrogen halide (to bring it into the basic form) and reuse it.

Weakly basic ion exchangers are regenerated typically with $NH_4OH$, $Na_2CO_3$ or NaOH. Precise instructions on this subject are provided by manufacturer's technical information sheets (for example Lewatit-Selective ion exchangers, Instructions for laboratory trials with Lewatit selective ion exchange resins, Technical Information, Bayer; Dow Liquid Separations, Dowex Marathon WBA, Ion Exchange Resin, Engineering Information, The Dow Chemical Company; Dowex Ion Exchange Resins, Properties, Impurities and Concentrations of Regenerant Chemicals).

Further information on the regeneration of ion exchangers can be found, for example, in: Regeneration of Anion Exchange Resins with Regular-Grade Diaphragm-Cell Caustic Soda: A Five-Year Plant Trial (IWC Proceedings, 10(88, S. D. Coker, M. P. Murphy); Petrochemical Company Anion Exchange Resin Regeneration Trial (Dow Report, 8/89, Michael A. Smith) and Caustic Soda for Ion Exchange Resin Regeneration (Marketing Research Report, 4/86, Ralph A. Bacon).

The present invention is illustrated in detail with reference to the figures FIG. 1 and FIG. 2 without the invention, whose scope of application is evident from the description and the claims, being restricted to these embodiments.

FIG. 1 shows one possible connection of reactors for a continuous mode. The process of FIG. 1 has three reaction steps. In the first step, a reactant A, for example a phosphorus trichloride, is fed into a reactor I which has an ion exchanger. Component K1 which is a first compound having an OH group is likewise metered into this reactor. The amount of component K1 is preferably such that there is a molar ratio of A to K1 of 3:1. The monoorganophosphorus dichloride obtained as the product B of the first reaction step I is transferred to the reactor II of the next reaction step which likewise has an ion exchanger. Also metered into this reactor is the component K2 which is a second compound having an OH group. The amount of component K2 is preferably in turn such that there is a molar ratio of B to K2 of 2:1 on entry into the reactor. The diorganophosphorus chloride obtained as the product C of the second reaction step II is transferred to the reactor III of the next reaction step which likewise has a basic ion exchanger. Also metered into this reactor is the component K3 which is a third compound having an OH group, for example a compound of the formula 24. The amount of component K3 is preferably such that there is a ratio of C to K3 of 1:1 on entry into the reactor. The product D obtained from reactor III is in the present case a phosphite which has a structrual unit T.

Figure 2:
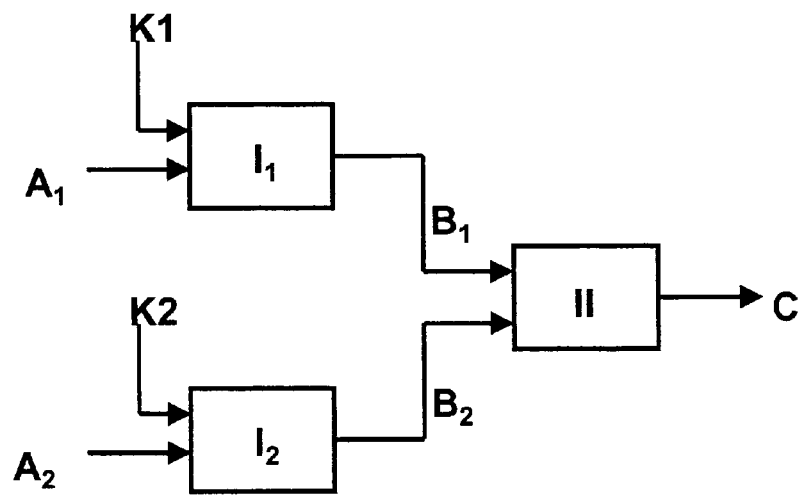

FIG. 2 shows another possible connection of reactors in which one process variant of the process according to the invention which has a plurality of reaction steps can be carried out continuously. Thus, the reactant $A_1$, for example a halodiorganophosphite of the formula 2, is fed together with the component K1, for example a dihydroxyl compound of the formula 22, in a ratio of 1:1, into reactor $I_1$ which has an ion exchanger. The reaction product $B_1$ obtained is a product of the formula 23. The reactant $A_2$, for example a compound of the formula O, is fed together with the component K2, for example a 2-hydroxybenzoic acid derivative T' in a ratio of 1:1, into reactor $I_2$ which likewise has an ion exchanger. The reaction product $B_2$ obtained is a product of the formula 17. The products $B_1$ and $B_2$ are conducted together, preferably in a molar ratio of 1:1, into the reactor II which likewise has a basic ion exchanger. In this reactor, the products $B_1$ and $B_2$ react to give product C of the formula 19 with elimination of hydrogen chloride.

The examples which follow are intended exclusively to illustrate the invention but not restrict its scope of application which is evident exclusively from the description and the claims.

EXAMPLES

All preparations were carried out under protective gas using standard Schlenk techniques. The solvents were dried before use over suitable desiccants. The ion exchanger used, Lewatit MP-62, was suspended in hexane to remove water and the water was removed azeotropically in a Dean-Stark apparatus.

Example 1

Preparation of 3-chloro-2,4-dioxa-3-phospha-phenanthren-1-one or 2-chloro-4H-naphtho[1,2-d]-1,3,2-dioxaphosphorine-4-one of the formula I

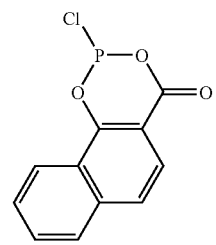

Example 1.1

Inventive, Using an Ion Exchanger

A mixture of 9.5 g (0.05 mol) of 1-hydroxy-2-naphthoic acid and 58 g (approx. 0.1 mol) of Lewatit MP 62 ion exchanger and 250 ml of toluene was stirred vigorously for 30 min, in the course of which the acid is gradually dissolved. Subsequently, a solution of 4.4 ml=6.9 g (0.05 mol) of phosphorus trichloride in 30 ml of toluene was added dropwise at room temperature, in the course of which gentle heat evolution took place. For workup, the solution was decanted from the ion exchanger, the residue was washed twice with approx. 80 ml of dried toluene and the solvent (toluene) was removed in an oil-pump vacuum. The product obtained was a colorless solid. The yield was 75% of theory.

Example 1.2

Comparative Example, Reaction in the Presence of Triethylamine

To a suspension of 18.82 g (0.1 mol) of 1-hydroxynaphthoic acid in 200 ml toluene was slowly added dropwise at 0° C. a solution of 42.2 ml (30.7 g; 0.3 mol) of triethylamine and 8.8 ml (13.9 g; 0.1 mol) of phosphorus trichloride in 30 ml of toluene, and the mixture was subsequently stirred. A colorless precipitate (amine hydrochloride) formed which complicated the stirring and subsequently made it impossible. Even addition of 100 ml of dried toluene could not make the suspension stirrable again. Subsequently, the reaction mixture was warmed to room temperature and left to react overnight. Afterward, the colorless solid was filtered off and washed 2× with 100 ml of toluene. The resulting clear solution was freed of volatile constituents in an oil-pump vacuum, and an oily residue was obtained. The crude product was dissolved again in toluene, and the precipitation of a colorless solid was observed. After repeated filtration, 18.6 g of a colorless solid were obtained. Yield: 74.35%.

For the same yield, the process according to the invention allows complicated removal of the base to be dispensed with. In addition, the process according to the invention succeeds in removing the base quantitatively, so that no traces of the base which could disrupt subsequent reactions are present.

Example 2

Preparation of 2-chloro-2,3-dioxa-2-phosphanaphthalin-4-one of the Formula II

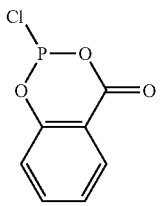

II

Example 2.1

Inventive, Using an Ion Exchanger

To a mixture of 1.38 g (0.01 mol) of salicylic acid and 11.7 g of MP62 Lewatit in 20 ml of toluene are added dropwise at room temperature 1.375 g (0.01 mol) of phosphorus trichloride. The reaction mixture is stirred for 15 min. A GC-MS investigation of the reaction solution shows complete conversion of the salicylic acid, and the desired product is formed with 100% selectivity.

Example 2.2

Comparative Example with Triethylamine

In a comparative experiment according to example 2.1 in which 0.02 mol of triethylamine was used instead of ion exchanger as a base, only 37% product formation was observed in the reaction under room temperature conditions. In addition, three further products which were not more precisely identified were formed.

Prior Art:

In Reaction product of phosphorus trichloride with salicylic acid; Cade, J. A.; Gerrard, W. *Chemistry & Industry* 1954, 402, the preparation of 2-chloro-4H-1,3,2-benzodioxaphosphorin-4-one with a yield of 85% is described, by reacting 1 mol of PCl₃, 1 mol of salicylic acid and 1 mol of pyridine in diethyl ether at −10° C.

In An examination of the reaction between phosphorus trichloride and salicylic acid. Young, Richard W., *Journal of the American Chemical Society* 1952, 74, 1672-3, 138 g of salicylic acid, 150 g of PCl₃ and 150 ml of toluene are boiled to reflux for 3 h, the toluene and PCl₃ are subsequently removed under reduced pressure and the residue is distilled. 120 g of 2-chloro-5,6-benzo-1,3,2-dioxaphosphorin-4-one were obtained, which corresponds to a yield of 59%.

It can easily be seen that the use of the weakly basic ion exchanger as a base enables a selectivity of 100%, which is enabled by none of the other processes.

Example 3

Phosphite of the formula III, prepared from 2,2'-bis (6-tert-butyl-1-hydroxy-4-methoxyphenyl) and phosphorus trichloride

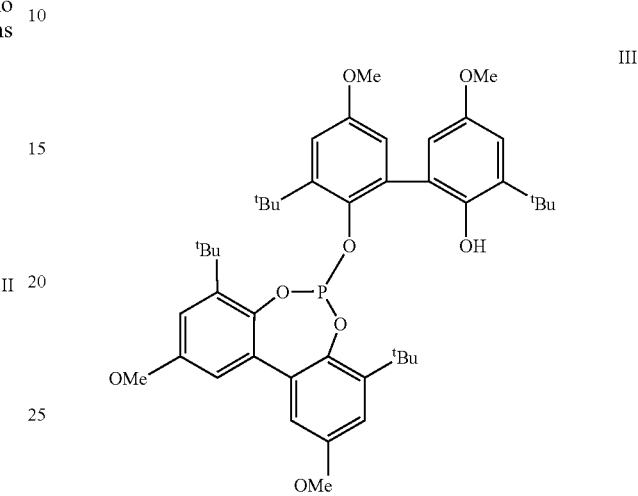

III

Example 3.1

Inventive

To a mixture of 26.5 g (0.045 molar eq.) of Lewatit MP-62 ion exchanger and 1.3 ml (2 g; 0.015 mol) of phosphorus trichloride in 200 ml of toluene was added dropwise with vigorous stirring at room temperature a solution of 12.3 g (0.03 mol) of 2,2'-bis(6-tert-butyl-1-hydroxy-4-methoxyphenyl) in 100 ml of toluene. Subsequently, the reaction mixture was heated to 60° C. for 2 h and cooled overnight. For workup, the ion exchanger was filtered off by means of a glass frit and washed 4 times with 50 ml of toluene. The solution was freed of volatile constituents at room temperature in an oil-pump vacuum, and the product was dried under reduced pressure. Yield: 11.8 g, corresponding to 93% of theory.

Example 3.2

Prior Art According to EP 1 201 675

To a solution of 2.42 g of 2,2'-bis(6-tert-butyl-1-hydroxy-4-methoxyphenyl) (6.75 mmol) and 1.6 ml of pyridine in 22 ml of THF is added dropwise at 0° C. a solution of 0.93 g of PCl₃ (6.75 mmol) in 10 ml of THF. After stirring at 25° C. for 4 h, the solvent is removed under reduced pressure. After adding 40 ml of diethyl ether, filtering and concentrating under reduced pressure, 2.8 g (98%) of spectroscopically pure chlorophosphorous ester of 2,2'-bis(6-tert-butyl-1-hydroxy-4-methoxyphenyl) are obtained. 2.8 g of this chloroester (6.62 mmol) in 20 ml of THF are added at room temperature to a monolithium phenoxide solution, obtained at −20° C., from 2.37 g of 2,2'-bis(6-tert-butyl-1-hydroxy-4-methoxyphenyl) (6.62 mmol) in 30 ml of THF and 20.7 ml of 0.32 M hexane solution of n-butyllithium (6.62 mmol). After 24 h, the mixture is concentrated under reduced pressure. Addition of 40 ml of methylene chloride, filtration and removal of the solvent under reduced pressure give 4.6 g (93%) of highly viscous product.

Use of Triethylamine as Described in the Prior Art (EP 0 213 639).

Approx. 179.2 g (0.5 mol) of 2,2'-dihydroxy-3,3'-di-t-butyl-5,5'-dimethoxy-1,1'-biphenyl are added to approx. 1600 ml of toluene. Sufficient toluene was then removed azeotropically in order to remove traces of moisture. The diol-toluene solution was then cooled to 80° C. and approx. 168.7 g (1.67 mol) of triethylamine were added. Approx. 68.7 g (0.5 mol) of $PCl_3$ were added to 200 ml of toluene. To this solution was added dropwise at −10° C. within 1 h and 40 min a diol-toluene solution. The reaction solution was kept at this temperature for a further 30 min. Subsequently, the solution was allowed to warm to room temperature within 2 h. Subsequently, the reaction mixture was filtered to remove the triethylamine hydrochloride precipitate and the precipitate was washed twice with 200 ml of toluene. The filtrate and the wash liquor were combined to give 717.5 g of solution of the phosphoochloridite intermediate in toluene.

Approx. 170 g of further 2,2'-dihydroxy-3,3'-di-t-butyl-5,5'-dimethoxy-1,1'-biphenyl were added to 800 ml of toluene. Subsequently, 48.1 g of triethylamine were added. The 717.5 g of the abovementioned phosphorochloridite-toluene solution were added to this solution at room temperature within 45 min. The temperature was increased to 80° C. for one hour and 45 minutes and then to 95° C. for 2 hours. Subsequently, the mixture was cooled to room temperature. Approx. 600 ml of distilled water were added to the reaction mixture in order to dissolve the solid triethylamine hydrochloride. After the solution had been given time to settle, the phases which formed were separated. The aqueous phase was extracted twice with 250 ml of toluene. The organic phase and the extracts were combined and dried over dry magnesium sulfate for one hour. Subsequently, the solution was filtered and concentrated under reduced pressure to give a solid residue. The residue was recrystallized with acetonitrile and 242.5 g (65.4% of theory) of the diorganophosphite were obtained.

As can be clearly seen with reference to the inventive example, the same yield can be obtained as in the prior art process, but the process control is distinctly simpler.

Example 4

Preparation of a Biphosphite of the Formula IV

IV

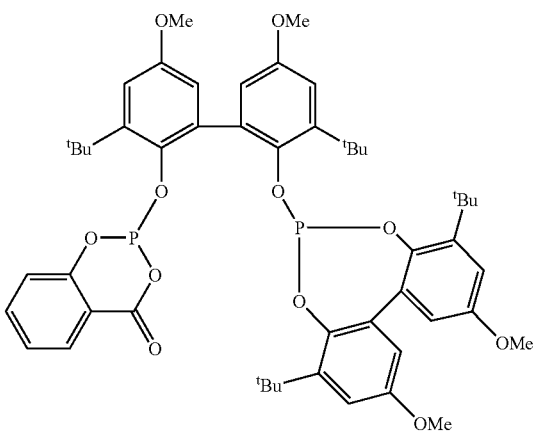

Example 4.1

Inventive

To a mixture of 32.4 g (0.055 mol) of MP-62 ion exchanger and 18.6 g (0.025 mol) of 2-[(3,3'-di-tert-butyl-5,5'-dimethoxy-1,1'-biphenyl-2,2'-diyl)phosphite]-2'-hydroxy-5,5'-dimethoxy-1,1'-biphenyl (Formula III) in 200 ml of toluene was added dropwise a solution of 6.09 g (0.03 mol) of 2-chloro-4H-1,3,2-benzodioxaphosphorin-4-one in 50 ml of toluene. Subsequently, the reaction mixture was stirred at 60° C. for 3 h. For workup, the ion exchanger was filtered off, toluene removed under reduced pressure and the residue recrystallized from acetonitrile. The yield was 61% at a purity of greater than 98%.

Example 4.2

Prior Art Acording to EP 1 201 675

Preparation of a Compound of the Formula III

To a solution of 2.42 g of 2,2'-bis(6-tert-butyl-1-hydroxy-4-methoxyphenyl) (6.75 mmol) and 1.6 ml of pyridine in 22 ml of THF is added dropwise at 0° C. a solution of 0.93 g of $PCl_3$ (6.75 mmol) in 10 ml of THF. After stirring at 25° C. for 4 h, the solvent is removed under reduced pressure. After adding 40 ml of diethyl ether, filtering and concentrating under reduced pressure, 2.8 g (98%) of spectroscopically pure chlorophosphorous ester of 2,2'-bis(6-tert-butyl-1-hydroxy-4-methoxyphenyl) were obtained; $^{31}P$ NMR ($CD_2Cl_2$) δ 172.7 ppm. 2.8 g of this chloroester (6.62 mmol) in 20 ml of THF are added at room temperature to monolithium phenoxide solution, obtained at −20° C., from 2.37 g of 2,2'-bis(6-tert-butyl-1-hydroxy-4-methoxyphenyl) (6.62 mmol) in 30 ml of THF and 20.7 ml of a 0.32 M hexane solution of n-butyllithium (6.62 mmol). After 24 h, the mixture is concentrated under reduced pressure. Addition of 40 ml of methylene chloride, filtration and removal of the solvent under reduced pressure give 4.6 g (93%) of highly viscous product.

Analysis (Cal. for $C_{44}H_{57}O_8P$=744.9 g/Mol) C 70.35 (70.95); H 7.86 (7.71). $^{31}P$ NMR ($CD_2Cl_2$) δ 140.7 ppm. $^1H$ NMR ($CD_2Cl_2$) δ 1.43 (s, 9 H); 1.56 (s, 9 H); 1.63 (s, 9 H); 1.67 (s, 9 H); 4.01 (s, 3 H);4.03 (s, 6 H); 4.05 (s, 3 H); 5.42 (s, 1 H); 6.7 . . . 7.3 (m, 8 H) ppm. FAB MS: m/e 745 (37%, M$^+$); 387 (100%, M$^+$-2,2'-bis(6-tert-butyl-1-hydroxy-4-methoxyphenyl)). IR (CHCl$_3$, 0.1 mm CaF$_2$), ν (OH)=3549 cm$^{-1}$.

Preparation of the Compound of the Formula IV

To a solution of 2.27 g of the compound of the formula III (9.19 mmol) in 72.5 ml of THF were added dropwise at −20° C. with stirring within 10 min 28.7 ml of a 0.32 molar solution of n-butyllithium (3.04 mmol). After warming to room temperature, the mixture is initially stirred for 30 min, and the resulting mixture is then added to 66.5 ml of a 0.138 molar solution of 2-chloro-1,3-dioxa-2-phosphanaphthalen-4-one (3.04 mmol) (Formula II prepared according to example 2) in THF. The reaction mixture was stirred at 25° C. for 4 h, the solvent was removed under reduced pressure and the syrup-like residue was stirred with 60 ml of hexane for 2 h. The mixture was filtered and washed twice with 7 ml of hexane, and the filtercake was extracted with hot hexane and with diethyl ether. After reducing the amount of solvent to one third and subsequently storing the solution at −20° C., the product is obtained in a 54% yield. $^{31}P$ NMR ($CD_2Cl_2$): 119.2 (m); 119.8 (m); 139.5 (m); 140.1 (m); $^1H$ NMR (CD$_2$Cl$_2$): 1.02 . . . 1.26 (36 H); 3.67 . . . 3.74 (12 H); 6.43 . . . 7.99 (12 H). FAB-MS: m/e 911 (100%, M$^+$), 744 (18%), 387 (13%).

As can be seen clearly with reference to example 4, the process according to the invention achieves distinctly better yields.

What is claimed is:

1. A process for preparing trivalent organophosphorus compounds which bear at least one structural unit S

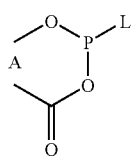
(S)

where A is a divalent substituted or unsubstituted alkyl or aryl radical which may form a ring system as per structural unit S, and the L radical is an organic radical bonded to the phosphorus atom via an oxygen or carbon atom, or is a halide, by condensing phosphorus compounds of the formula i

(i)

where Hal is halide selected from chlorine, bromine and iodine, and the halides may be the same or different, R is an organic radical bonded to the phosphorus via a carbon or oxygen atom, and a=2 or 3, with an organic compound of the formula S'

(S')

where A is as defined for the structural unit S,
which comprises
carrying out the reaction in the presence of at least one basic ion exchange resin.

2. The process of claim 1,
wherein
trivalent organophosphorus compounds which have at least one structural unit T

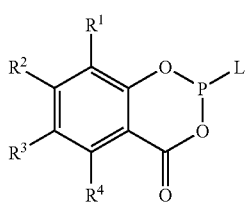
(T)

where R$^1$, R$^2$, R$^3$, and R$^4$ are each independently selected from monovalent substituted and unsubstituted aliphatic, alicyclic, aromatic, heteroaromatic, mixed aliphatic-alicyclic, mixed aliphatic-aromatic, heterocyclic, mixed aliphatic-heterocyclic, hydrocarbon radicals having from 1 to 50 carbon atoms, H, F, Cl, Br, I, —CF$_3$, CH$_2$(CF$_2$)$_j$CF$_3$ with j=0-9, —OR$^9$, —COR$^9$, —CO$_2$R$^9$, —CO$_2$M, —SR$^9$, —SO$_2$R$^9$, —SOR$^9$, —SO$_3$R$^9$, —SO$_3$M, —SO$_2$NR$^9$R$^{10}$, —NR$^9$R$^{10}$, —N=CR$^9$R$^{10}$, where R$^9$ and R$^{10}$ are each independently selected from H, monovalent substituted and unsubstituted aliphatic and aromatic hydrocarbon radicals having from 1 to 25 carbon atoms, and M is an alkali metal ion, formally half an alkaline earth metal ion, ammonium ion or phosphonium ion, or adjacent R$^1$ to R$^4$ radicals together form a fused substituted or unsubstituted aromatic, heteroaromatic, aliphatic, mixed aromatic-aliphatic or mixed heteroaromatic-aliphatic ring system; and the substituted hydrocarbon radicals may have as substituents those selected from —N(R$^5$)$_2$, —NHR$^5$, —NH$_2$, fluorine, chlorine, bromine, iodine, —OH, —CN, —C(O)—R$^5$, —C(O)H or —C(O)O—R$^5$, —CF$_3$, —O—R$^5$, —C(O)N—R$^5$, —OC(O)—R$^5$ and/or —Si(R$^5$)$_3$, where R$^5$ is a monovalent hydrocarbon radical preferably having from 1 to 20 carbon atoms, and, when a plurality of hydrocarbon radicals R$^5$ is present, they may be the same or different, and R$^1$, R$^2$, R$^3$ and R$^4$ radicals may be the same or different, and L is an organic radical bonded to the phosphorus atom via an oxygen or carbon atom, or is a halide, are prepared by condensing phosphorus compounds of the formula i

(i)

where Hal is halide selected from chlorine, bromine and iodine, and the halides may be the same or different, R is an organic radical bonded to the phosphorus via a carbon or oxygen atom and a=2 or 3, with an organic compound of the formula T'

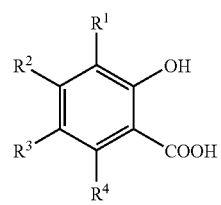
(T')

where the R$^1$ to R$^4$ radicals are each as defined for the structural unit T.

3. The process of claim 1,
wherein
the trivalent organophosphorus compound prepared is at least one compound selected from the compounds of the following formulae

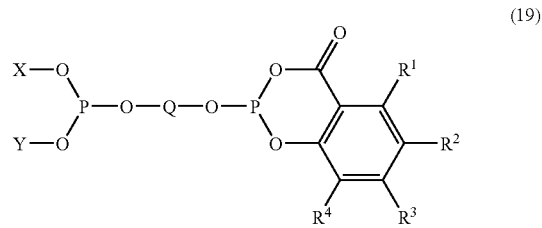
(19)

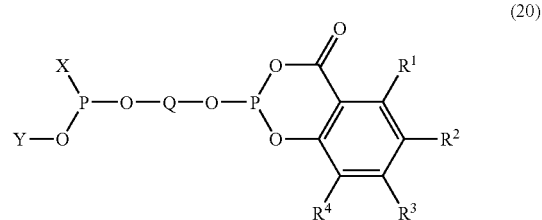
(20)

-continued

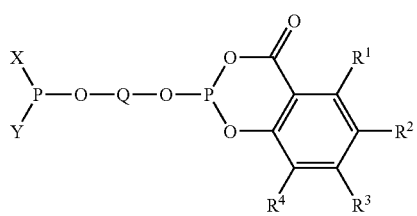
(21)

where X and Y are substituted or unsubstituted, aliphatic, alicyclic, aliphatic-alicyclic, heterocyclic, aliphatic-heterocyclic, aromatic-aromatic or aliphatic-aromatic hydrocarbon radicals having from 1 to 50 carbon atoms, and X and Y are the same or different or covalently joined together, and where Q is an at least divalent, substituted or unsubstituted aliphatic, alicyclic, aliphatic-alicyclic, heterocyclic, aliphatic-heterocyclic, aromatic, aromatic-aromatic or aliphatic-aromatic hydrocarbon radical, and the substituted hydrocarbon radicals may have as substituents those selected from —N($R^5$)$_2$, —NHR$^5$, —NH$_2$, fluorine, chlorine, bromine, iodine, —OH, —CN, —C(O)—R$^5$, —C(O)H or —C(O)O—R$^5$, —CF$_3$, —O—R$^5$, —C(O)N—R$^5$, —OC(O)—R$^5$ and/or —Si($R^5$)$_3$, where R$^5$ is a monovalent hydrocarbon radical preferably having from 1 to 20 carbon atoms, and, when a plurality of hydrocarbon radicals R$^5$ is present, they may be the same or different, and where R$^1$ to R$^4$ are each as defined for the structural unit T.

4. The process of claim 1, wherein
the trivalent organophosphorus compounds prepared are phosphites of the formula 10 or 11

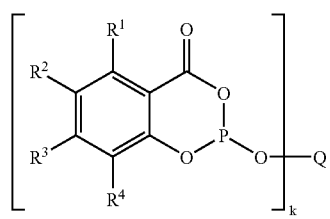
(10)

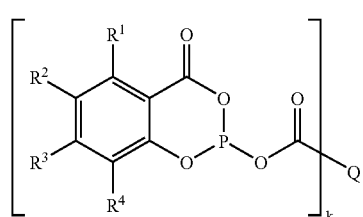
(11)

where R$^1$, R$^2$, R$^3$, and R$^4$ are each as defined for the structural unit T, Q is a k-valent substituted or unsubstituted aliphatic, alicyclic, mixed aliphatic-alicyclic, heterocyclic, mixed aliphatic-heterocyclic, aromatic, heteroaromatic, mixed aliphatic-aromatic, hydrocarbon radical having from 1 to 50 carbon atoms, and aliphatic moieties of Q may contain oxygen, sulfur and/or nitrogen, and where the substituted hydrocarbon radicals may have as substituents those selected from —N($R^5$)$_2$, —NHR$^5$, —NH$_2$, fluorine, chlorine, bromine, iodine, —OH, —CN, —C(O)—R$^5$, —C(O)H or —C(O)O—R$^5$, —CF$_3$, —O—R$^5$, —C(O)N—R$^5$, —OC(O)—R$^5$ and/or —Si($R^5$)$_3$, where R$^5$ is a monovalent hydrocarbon radical preferably having from 1 to 20 carbon atoms, and, when a plurality of hydrocarbon radicals are R$^5$ is present, they may be the same or different, k is at least 2, and R$^1$, R$^2$, R$^3$ and R$^4$ in the individual structural elements T bonded to Q may each have the same or different definitions.

5. The process of claim 1, wherein
the phosphorus compound of the formula i used is at least one compound selected from the compounds of the following formulae

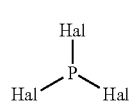
(0)

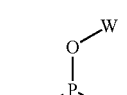
(1)

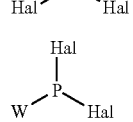
(6)

where W is an organic radical.

6. The process of claim 5, wherein
the phosphorus compound of the formula i used is a compound of the formula 1 which is prepared by reacting a compound 0 with an organic compound having at least one hydroxyl group W in the presence of a basic ion exchanger.

7. The process of claim 6, wherein
the compound having at least one hydroxyl group W is at least one substituted or unsubstituted compound selected from methanol, ethanol, n-propanol, isopropanol, 1-butanol, 2-butanol, t-butanol, 2-ethylhexanol, isononanol, isodecanol, isotridecanol, phenol, phenol derivatives, 1,4-dihydroxybenzene, 1,2-dihydroxybenzene, 1,8-dihydroxynaphthalene, 1,1'-binaphthyl-2,2'-diol, 2,2'-binaphthyl-1,1'-diol, or a compound which has one or more hydroxyl groups and one or more of the structural units T, and the substituted compounds have substituents selected from primary, secondary and tertiary alkyl groups, alicyclic groups, aromatic groups, —N($R^5$)$_2$, —NHR$^5$, —NH$_2$, fluorine, chlorine, bromine, iodine, —OH, —CN, —C(O)—R$^5$, —C(O)H or —C(O)O—R$^5$, —CF$_3$, —O—R$^5$, —C(O)N—R$^5$, —OC(O)—R$^5$ and/or —Si($R^5$)$_3$, where R$^5$ is a monovalent hydrocarbon radical preferably having from 1 to 20 carbon atoms, and, when a plurality of hydrocarbon radicals R$^5$ is present, they may be the same or different.

8. The process of claim 6, wherein
compounds of the formula 1 are prepared by in each case initially charging the phosphorus compound together with one or more basic ion exchange resins and subsequently metering in the compound having at least one OH group.

9. The process of claim 3, wherein asymmetric diphosphorus compounds of the formulae 19, 20, 21, are prepared by initially charging the compound having OH groups together with one or more basic ion exchange resins and subsequently metering in one or more phosphorus compounds.

10. The process of claim 1, wherein the reaction of a compound having at least one phosphorus-halogen bond with a compound having at least one hydroxyl group is one reaction step.

11. The process of claim 1, wherein, when carrying out a plurality of reaction steps, they may be carried out continuously or batchwise.

12. The process of claim 11, wherein, when carrying out a plurality of reaction steps, identical or different ion exchangers may be used in the reaction steps.

13. The process of claim 11 wherein, when carrying out the plurality of reaction steps, identical or different temperatures may be set in the reaction steps.

14. The process of claim 1, which is carried out in the presence of one or more solvents which are selected from the group consisting of benzene, toluene, xylene, pentane, n-hexane, n-heptane, cyclohexane, methylcyclohexane, diethyl ether, diisopropyl ether, methyl tert-butyl ether, anisole, tetrahydrofuran, 1,4-dioxane, 1,3-dioxolane, ethyl acetate, isobutyl acetate, tert-butyl acetate, ethylene carbonate, propylene carbonate, 1,2-butylene carbonate, acetone, 2-butanone, 3,3-dimethyl-2-butanone, benzonitrile, propionitrile, acetonitrile, lactones, N-methylpyrrolidone, dimethylformamide, dimethyl sulfoxide, N-alkylmorpholines, amines and sulfolane.

15. The process of claim 1, which is carried out in the presence of polymeric, weakly basic ion exchange resins based on styrene-divinylbenzene copolymers which bear N,N-diakylamine groups.

16. The process of claim 15, wherein the ion exchanger is used in the form of particles having an average particle size of from 10 μm to 2 mm or in the form of a fixed package.

17. The process of claim 15, wherein the ion exchanger is dried before use in the process according to the invention.

18. The process of claim 1, which is carried out in the presence of a proton transferrer.

* * * * *